US006769546B2

(12) United States Patent
Busch

(10) Patent No.: US 6,769,546 B2
(45) Date of Patent: Aug. 3, 2004

(54) EPIDURAL ANESTHESIA KIT

(76) Inventor: L. John Busch, 907-B Medical Centre, Fort Worth, TX (US) 76012

( * ) Notice: Subject to any disclaimer, the term of this patent is extended or adjusted under 35 U.S.C. 154(b) by 33 days.

(21) Appl. No.: 10/189,708

(22) Filed: Jul. 3, 2002

(65) Prior Publication Data

US 2004/0004019 A1 Jan. 8, 2004

(51) Int. Cl.[7] .............................................. B65D 69/00
(52) U.S. Cl. ........................ 206/571; 206/440; 206/366
(58) Field of Search ................................ 206/570–572, 206/223, 232, 363–366, 564, 438, 440, 400; 504/28, 93.01, 158, 161, 355, 541

(56) References Cited

U.S. PATENT DOCUMENTS

| | | | | | |
|---|---|---|---|---|---|
| 3,851,649 | A | * | 12/1974 | Villari | 206/571 |
| 4,226,328 | A | * | 10/1980 | Beddow | 206/571 |
| 4,523,679 | A | * | 6/1985 | Paikoff et al. | 206/570 |
| 4,614,183 | A | | 9/1986 | McCracken et al. | |
| 4,795,441 | A | * | 1/1989 | Bhatt | 206/364 |
| 4,917,238 | A | * | 4/1990 | Schumacher | 206/570 |
| 4,928,830 | A | * | 5/1990 | Brewer | 206/570 |
| 4,954,239 | A | * | 9/1990 | Mueller | 206/571 |
| 5,085,631 | A | | 2/1992 | Leighton | |
| 5,178,282 | A | * | 1/1993 | Williams | 206/570 |
| 5,311,990 | A | * | 5/1994 | Kalinski | 206/570 |
| 5,470,318 | A | | 11/1995 | Griffith, III et al. | |
| 5,779,053 | A | * | 7/1998 | Partika et al. | 206/570 |
| 6,123,193 | A | | 9/2000 | Vojtasek et al. | |
| 6,228,324 | B1 | * | 5/2001 | Hasegawa et al. | 206/364 |
| 6,579,271 | B1 | * | 6/2003 | Aruffo et al. | 206/570 |
| 2002/0185406 | A1 | * | 12/2002 | Massengale et al. | 206/571 |

OTHER PUBLICATIONS

Product information cover sheet for B–D Perisafe Epidural Anesthesia Tray (#407516) by Becton–Dickinson, Franklin Lakes, NJ. Date unknown, but at least by Mar. 2002.
Product Information cover sheet for Baxter Continuous Epidural Anesthesia Tray (#1T5872) by Baxter Healthcare Corp. Deerfield, IL. Date unknown but at least by Mar. 2002.
Product Information cover sheet for Baxter Continuous Epidural Anesthesia Tray (#1T2673) by Baxter Healthcare Corp. Deerfield, IL. Date unknown but at least by Mar. 2002.
Product Information cover sheet for ARROWgard Blue Plus Multi–Lumen CVC Super Kit (AK–45703–SK) by Arrow Int'l., Inc., Reading, PA, Date unknown but at least by Mar. 2002.
Samuel C. Hughes, Gershon Levinson, Mark Rosen, Shnider and Levinson's Anesthesia for Obstetrics, Chapter 8, pp. 123–144, (2002).
Mark Norris, Obstestric Anesthesia, Chapter 15, pp. 293–311, (1999).

* cited by examiner

Primary Examiner—Luan K. Bui
(74) Attorney, Agent, or Firm—Grady K. Bergen; Robert H. Johnston, II

(57) ABSTRACT

An epidural anesthesia kit preferably includes a skin-preparation package that is readily accessible before having to unfold a packaging towel, a plurality of pre-filled syringes, and a cup having a removeable lid for quick access to saline or other injectable fluid. Methods of manufacturing such kits and using them are also provided.

16 Claims, 2 Drawing Sheets

EPIDURAL ANESTHESIA KIT

TECHNICAL FIELD OF THE INVENTION

The present invention relates to administering anesthesia to patients and more particularly to an improved epidural anesthesia kit and method.

BACKGROUND OF THE INVENTION

Epidural anesthesia is a common neuraxial analgesia for labor and other procedures. In delivering epidural anesthesia, the healthcare provider desires safely and efficiently to provide the anesthesia to the patient. This form of anesthesia is most frequently used with women who are in labor, but a number of other uses exist as well.

The use of epidural anesthesia is well established and various approaches have been documented. See generally, Samuel Hughes, Gershon Levinson, and Mark Rosen, eds., *Shnider and Levinson's Anesthesia for Obstetrics* (Philadelphia: Lippincott, Williams & Wilkins, 2002) and Mark Norris, ed., *Obstetric Anesthesia* (Philadelphia: Lippincott, Williams & Wilkins, 1999). The technique suggested in Shnider and Levinson's text involves the steps that follow.

After a number of preliminary steps are taken, the patient is positioned, the back of the patient is washed with an appropriate antiseptic solution, and the lumbar area is draped. The lumbar spinous processes are palpated and the widest interspace is selected below L3. An epidural needle is then used to locate the epidural space using a midline approach or lateral or paramedian approach. Typically the loss-of-resistance technique is used with a saline-filled or air-filled syringe to identify the likely location of the epidural needle during placement. Once the needle is placed, one aspirates for blood or cerebrospinal fluid. The catheter is then placed through the needle. A free saline or dilute local anesthetic may be used to facilitate the passage of the catheter.

After the catheter is inserted, the needle is removed and a test dose is usually administered; the text describes it this way: "Use of a 3-mL test dose of a local anesthetic containing epinephrine 1:200,000 (5 $\mu g \cdot mL^{-1}$) is most common. Observe for heart rate increase within 60 sec. or evidence of spinal blockade within 3–5 min. If test dose is negative, administer additional drug in divided doses as required to obtain desired pain relief." After this, certain follow-up steps are suggested.

Numerous kits are available for administering epidural anesthesia. One of the many possible examples is the Baxter® Continuous Epidural Anesthesia tray (Model 1T2673). This kit contains a plastic tray container that is sealed with a top sheet that can be removed. Once it is removed all the items inside the tray are resting upon a large towel blanket that is folded around the contents, i.e., the contents are wrapped in the towel. When the towel (or blanket) is opened one finds another towel to be used and a drape. Once those are removed there is a first subtray that contains three gauze sponges and a package of a skin preparation solution (Providone iodine solution USP, 10% Providone iodine, Titratable iodine 1%). Under that subtray there is another subtray or procedural tray that contains the following items: A glass vial with 1.5% Lidocaine Hydrochloride injection, and Epinephrine 1:200,000, 5 mL (for test dose); 1% lidocaine Hydrochloride injection, USP 5 mL; 0.9% Sodium Chloride injection, USP, 10 mL; mixing cups; syringe, 3 cc with needle, 18 ga.×3.8 cm; needle, 25 ga.×2.5 cm; needle, 22 ga.×3.8 cm; needle, filter aspirating, 19 ga.×3.8 cm; procedure filter, 0.22 microns; sharp's stickpad, a catheter connector; a catheter support pad; a syringe, 20 cc; syringe tip and catheter connector; protectors; fenestrated drape; and an epidural caution label.

In using a kit like this one, the top level of the package is first opened and the towel that surrounds everything is unfolded to reveal the contents. The skin-preparation subtray is removed and set out. The skin preparation solution is opened and poured into a compartment of the skin-prep subtray, and then the gauze sponges are dipped and used to prepare the skin. The skin-preparation solution must typically be placed on the skin a certain period of time before other steps can be taken in the procedure. With respect to preparing other implements, the healthcare provider breaks the vial containing the local anesthetic, i.e., the tip of it is literally broken off by hand. This—as with the breaking of other glass vials—can lead to the healthcare provider cutting himself or herself on the glass. The local anesthetic can be loaded into a syringe using a filter needle to address concerns about any glass being in the anesthetic. Then the filter needle is replaced by a hypodermic needle, and then the patient's skin can be punctured and the local anesthetic delivered.

Assuming a loss-of-resistance technique is being used with saline, the vial containing saline (sodium chloride) must be broken off and then the saline is placed in the epidural syringe. Then the epidural needle (Tuohy, Crawford, etc.) is attached. The needle is placed in the epidural space. A test does may be given to help confirm placement of the needle. To administer the test dose, a glass vial with the test dose is broken, filtered, and loaded into a syringe and administered. Once the test satisfies the healthcare provider that the needle is properly placed, a catheter may be placed and an initial loading dose can be administered. The epidural catheter may be placed through the epidural needle and put into the proper location and then the epidural needle removed. If a continuous epidural anesthesia is to be applied, the catheter is then attached to the appropriate equipment. With all the preparations and steps, this can be a lengthy process.

In anesthesia kits in general, the skin preparation components are typically in a tray as discussed above. One recent kit secures the skin preparation package by placing it in an interior fold of an outer towel. In this kit, AGB's ARROWgard Blue plus™ Multi-Lumen CVC Super Kit (AK-45703-SK) by Arrow International of Reading, Pa., a 1-step applicator (CHLORAPREP®) is found inside a first or second fold of the exterior towel. When accessing the 1-step applicator, the healthcare provider opens the package and has to unfold the external towel at least partially to access the skin preparation unit, and then with one or two more folds the remainder of the kit is accessed as well.

Improvements remain desirable—especially for epidural blocks. Particularly of interest are improvements in the safety of the procedure and kits as well as any timesaving devices or steps.

SUMMARY OF THE INVENTION

Therefore, a need has arisen for an improved epidural anesthesia kit and method that address shortcomings of previous epidural processes and kits.

According to an aspect of the present invention, an epidural kit for quickly administering epidural anesthesia to a patient includes a packaging towel; a skin preparation package that is ready to be opened and used to prepare a patient's skin for penetration by needles before having to further open the kit; a first syringe pre-filled with a local anesthetic; an epidural needle for locating an epidural space of a patient; a catheter for positioning in the epidural space of a patient through the epidural needle; a second syringe pre-filled with a test fluid; a preloaded cup having a removable lid and filled with a saline solution; a tray for holding and removeably securing the first and second syringes, epidural needle, and saline cup; and a package for enclosing the tray in a sterile environment.

According to another aspect of the present invention, an anesthesia kit includes an outer tray; a packaging towel disposed within an interior portion of the outer tray; a plurality of syringes disposed within the outer tray and on the interior of the packaging towel; and a skin-preparation package located on the exterior of the packaging towel to provide for access to the skin-preparation package without requiring access to the interior of the packaging towel.

According to another aspect of the present invention, an anesthesia kit includes an outer tray; a packaging towel disposed within an interior portion of the outer tray; a skin preparation package secured relative to the outer tray; and a plurality of syringes pre-filled with an injectable fluid and disposed within the outer tray and on an interior of the packaging towel.

According to another aspect of the present invention, an anesthesia kit includes an outer tray; a packaging towel disposed within an interior portion of the outer tray; a cup having a removeable, sealed lid and containing an injectable fluid; and a plurality of syringes disposed within the outer tray and on the interior of the packaging towel.

According to another aspect of the present invention, a method of manufacturing an epidural anesthesia kit includes the steps of providing an outer tray; providing an inner-tray having compartments for holding objects secure; filling a local anesthetic syringe; filling a test-dose syringe; placing the local and test-dose syringes into the inner-tray; filling a cup with saline and sealing it with a removeable lid; placing the saline cup in the inner tray; placing an epidural syringe, catheter, and epidural needle on the inner tray; placing the inner-tray on a packaging towel; placing the packaging towel in the outer tray; folding the packaging towel about the inner tray; sealing the top portion of the outer tray with a top-sealing sheet; and removeably securing a skin-preparation package to an outer portion of the packaging towel or an outer portion of the top sheet so that the skin-preparation package may be accessed without requiring the packaging towel to be unfolded.

According to another aspect of the present invention, a method of administering an epidural block using an epidural kit includes opening the anesthesia kit and accessing a skin-preparation package before unpackaging the remainder of the kit, using a plurality of pre-loaded syringes, and using a pre-filled saline cup.

The present invention provides advantages, and a few examples follow. An advantage of the present invention is that it allows for faster implementation of epidural anesthesia—something both the patient and healthcare provider want. Another advantage is that the present kit and method enhance safety by removing any risk of injury to the healthcare provider's hands due to broken glass vials as well as any risk of glass shards remaining in any of the liquids administered to the patient.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

The preferred embodiment of the present invention and its advantages are best understood by referring to FIGS. 1–4 of the drawings, like numerals being used for like and corresponding parts of the various drawings.

Figure 1:
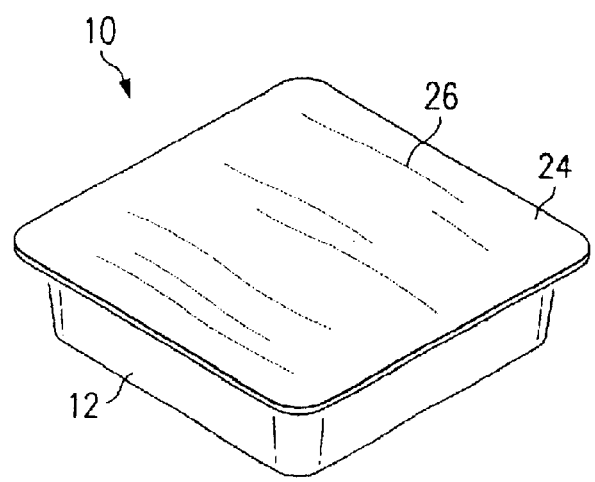
FIG. 1 is a schematic, perspective view of an anesthesia epidural kit according to the present invention.
Figure 3:
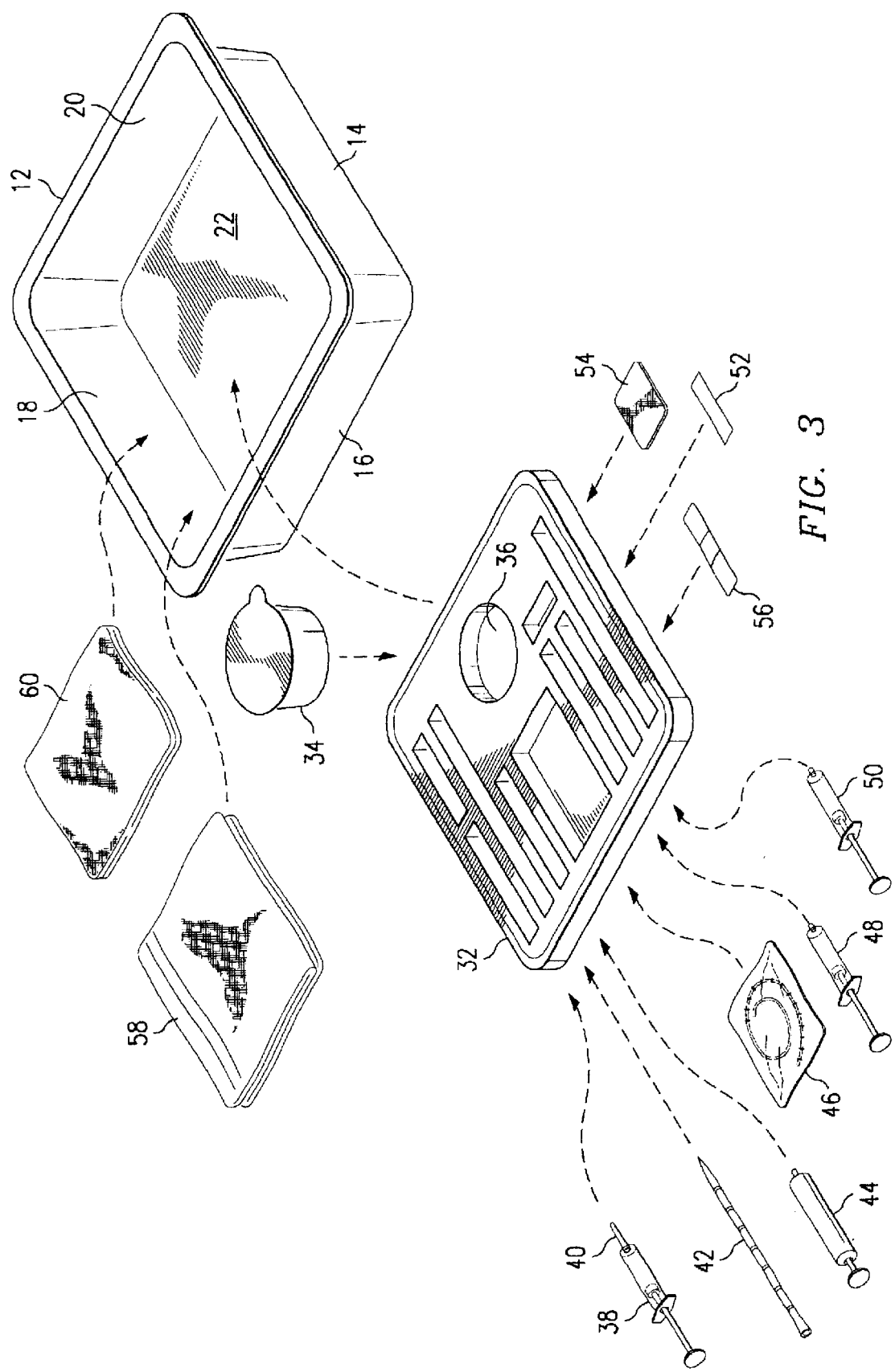
FIG. 3 is a schematic, perspective view of the interior tray or subtray of the kit of FIGS. 1–2 with various illustrative components that accompany the tray.

Referring to FIG. 1, a prepared epidural kit or packaged tray 10 according to one embodiment of the present invention is shown. Kit 10 has an outer tray 12 formed with four sidewalls 14, 16, 18, 20 and a bottom 22 (FIG. 3). Outer tray 12 is preferably formed of plastic. A top opening formed by the four walls is shown sealed with a top-sealing sheet 24, which is preferably made from a strong, but pliable material, such as a TYVEK® material. The top-sealing sheet 24 would typically have visual indicia 26 printed on it, such as descriptions of how to use the product and its contents.

Figure 2:
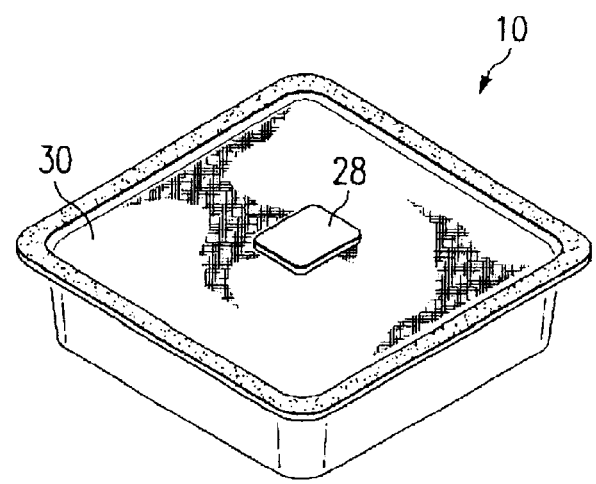
FIG. 2 is the kit of FIG. 1 with the top-sealing sheet removed.

Referring to FIG. 2, the epidural kit 10 is shown with top-sealing sheet 24 removed. As an important aspect of the present invention, a skin-preparation package 28 is immediately available upon removing the top sheet 24. Thus, it is shown resting on top of folded packaging towel 30. The skin-preparation package 28 preferably contains a presoaked preparation swab, sponge, applicator, or the like, that is soaked in Betadine or another antiseptic solution (e.g., alcohols, idophors, chlorhexadine, chlorhexadine gluconate with isopropyl alcohol, etc.). Use of certain skin preparation solutions, such as 2% chlorhexidine gluconate with 70% isopropyl alcohol may allow quicker drying times—on the order of 30 seconds—compared to Betadine which may require minutes. By having the skin-preparation package 28 immediately available upon removal of the top sheet 24, the healthcare provider can immediately open the package 28 and prepare the patient's skin. This will allow the skin-preparation solution on it to begin drying while the healthcare provider continues to set up the remaining items in kit 10 for administration to the patient.

Referring now to FIG. 3, the preparation of other components of kit 10 are shown by an assembly schematic. To go from the kit as shown in FIG. 2 to the kit as shown in FIG. 3, the following steps have been carried out: the skin preparation package 28 has been removed and holding, or packaging, towel 30 has been unfolded and in this particular figure removed with all of its contents likewise removed but shown outside of the package.

The interior tray or subtray 32 rests inside the outer tray 12 and on the packaging towel 30 when the kit 10 is in its packaged position. Subtray 32 is, for example, a blown plastic tray with molded compartments to hold each of the components, such as needles and cup 34, in a secure position while waiting for kit 10 to be used. As one specific example, the rounded sealed cup 34 corresponds with the round receiving compartment 36 in subtray 32, and thereby, is held secure during transportation and storage. In a similar fashion, the other components that are at risk of moving or being damaged in some way during transport and storage have compartments designed to hold them secure.

The subtray 32 holds a preloaded syringe with local anesthetic 38 that has a corresponding hypodermic needle 40. To facilitate quick identification of the local anesthetic syringe 38, the needle 40 may already be attached, but an additional turn of the needle may be required to break a seal. Of course, an epidural needle 42 is provided and is shown in its covering. An epidural syringe 44 is included. An epidural catheter in its package 46 is provided. As previously mentioned, a sealed cup 34, which in this embodiment contains saline, is provided. Cup 34 will be described in more detail in connection with FIG. 4. A syringe 48 that is pre-loaded or pre-filled with a test dose of a test fluid (e.g., local anesthesia with epinephrine) is provided. An initial epidural anesthesia load is in pre-loaded syringe 50. In addition, while not explicitly shown, there are a variety of needles that may be used with syringes 48 and 50. The kit 10 may include additional items such as a label 52, which makes it clear that the catheter should only be used for epidural anesthesia; a gauze 54; additional syringes; and a securing bandage 56. In addition, a roll of tape for securing the catheter to the patient may also be provided. With respect to bandage 56, it is desirable to secure the catheter 46 in place, but to also provide the ability conveniently to observe the site where the catheter enters the patient, and this can be done by using a clear bandage such as a BIOCLUSIVE® bandage from Johnson & Johnson Medical of Arlington, Tex. (see U.S. Pat. No. 4,614,183, which is incorporated by reference for all purposes).

Each item either rests in its respective compartment in subtray 32 or on top of subtray 32. Subtray 32 is placed on top of an interior portion of towel 30 that is placed into an interior of the outer tray 12. A drape 58 and one or more additional towels 60 may be placed on top of subtray 32. The towel 30 may then be folded closed and the skin-preparation package 28 placed on top of the towel before the top-sealing sheet 24 is applied and sealed. It some instances it may be desirable to secure the skin-preparation package 28 to the towel 30 using an adhesive or tape or other means. Also, in an alternative embodiment, the skin-preparation package could be sealed and removeably attached to an exterior of the sealing sheeting 24. Either way, the skin-preparation package should be accessible without requiring towel 30 to be unfolded.

Figure 4:
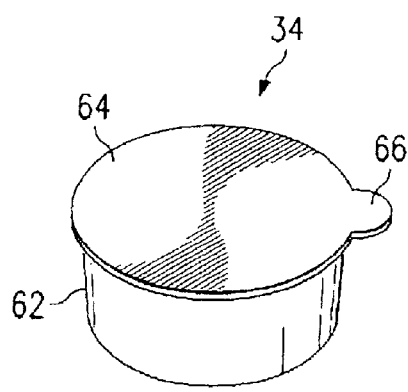
FIG. 4 is a schematic perspective view of a sealed container for use according to an aspect of the present invention.

Referring to FIG. 4, a solution is provided in a plastic container or cup 34 that preferably has circular sidewalls 62 and a removable lid 64. Cup 34 could take other shapes. The overall shape of cup 34 is, preferably, similar to a salad-dressing container used on many commercial airliners. Lid 64 preferably has a tab portion 66, and when it is desirable to use the fluid in cup 34, tab 66 is pulled by the healthcare provider using his or her fingers to remove or partially remove the top 64 to allow access to the fluid in cup 34. Cup 34 could also have a screw off cap in an alternative embodiment. In the case of a preferred epidural kit, cup 34 holds a saline solution. In some applications, cup 34 might hold any injectable fluid, e.g., heprinized saline, sterile water, dye, radio opaque substances, a test dose such as a local anesthesia with Epinephrine, and anesthesia. Furthermore, a plurality of cups 34 might be included in a kit 10—each with a different injectable fluid. In the latter situation, the cups 34 allows these fluids to be quickly loaded—again without having to break open any vials and without necessarily requiring a needle to be attached.

With reference to FIGS. 1–4, one illustrative method of using kit 10 is now described. Beginning with a prepared kit 10 as in FIG. 1, the kit 10 is placed out on a surface and the top-sealing sheet 24 is removed. With the patient in the proper position, the skin preparation package 28 is opened and the skin preparation solution is used to prepare the patient's skin in the area that is to be punctured. While the skin-preparation solution dries or remains for a prescribed period of time on the patient, the towel 30 is unfolded exposing the interior contents of tray 12. Preloaded syringe 38 is obtained and, if not already attached, needle 40 is attached to it. Syringe 38 is prefilled with a local anesthesia (e.g., Bupivacaine, Ropivacaine, Lidocaine, 2-Chloroprocaine, etc.). The local anesthesia is then administered to the patient.

If a saline solution is desired to be used for tactile feedback in the loss-of-resistance technique, the epidural syringe 44 is filled with saline from cup 34, which has had the lid 64 pulled back. The epidural needle 42 is attached to the syringe 44. The healthcare provider places the epidural needle into the epidural space of the patient using proper techniques and precautions, and then syringe 44 may be removed and catheter package 46 opened and applied into needle 42. Once the catheter is in place, a preloaded syringe 48 may be used with the catheter to administer a test dose (e.g., local anesthetic with epinephrine). Once the test dose has been administered and the healthcare provider is satisfied that the epidural needle 42 is in its proper location, a preloaded load of epidural anesthesia may be administered by using preloaded syringe 50.

Once catheter 46 is in place, the catheter 46 may be secured by using adhesive bandage 56. Label 52 may be used to appropriately label the epidural catheter. Tape may be used to further secure the catheter 46 to the patient. The catheter 46 may be attached to proper equipment to provide a continuous epidural if desired.

This kit 10 and the associated method enhance safety for all involved and save time. The improved safety and time-savings are due primarily to three important features. First, the skin-preparation package is immediately accessible upon opening the kit 10 (or even before). This avoids the need to perform additional unpacking of the kit before the skin preparation package is accessed and applied. This in turn allows the prescribed drying time to begin sooner. Furthermore, there is no requirement that the skin-preparation package be poured into a subtray and then a swab doused or anything else of that nature. Thus, the swab of the current design may be administered immediately and it can be drying while the rest of the contents of the kit are accessed. Second, once inside kit 10, the syringes are preloaded with the anesthesia and test doses to be used. This provides timesavings in not having to break open glass vials and apply any filtering needles or to take the time to aspirate the proper amount of substance into each syringe. Finally, the pre-loaded cup 34 allows for a fluid, such as saline, to be quickly accessed and to be readily aspirated without even the need for a needle and does not pose any risk of glass shards. As shown by the chart below, these three features combine to improve the time involved in the procedure. The features may be used alone as well to great advantage.

While clinical testing of the kit has not yet been performed, the timesavings are estimated to be on the order shown in the chart below.

| Step | Estimated Time Savings for an Epidural |
| --- | --- |
| 1. Immediate access of skin-prep | 1 min. |
| 2. Pre-loaded Local | 30 sec.–1 min. |
| 3. Pre-filled saline cup | 15–30 sec. |
| 3. Pre-loaded Test dose | 30 sec. |
| 4. Pre-loaded Load Dose | 20–30 sec. |
| Total | 2:35–3:30 minutes |

Thus, the estimated timesavings are up to 3 and half minutes per epidural block administered. Given that operating rooms can be as expensive as $30 to $80 a minute, this represents significant money savings to the hospital. More importantly, in the case of the laboring woman, it represents quicker pain relief. Finally, for the healthcare provider, it allows more efficient and safer deliver of epidural anesthesia.

Although the present invention and its advantages have been described in detail, it should be understood that various changes, substitutions and alterations can be made therein without departing from the spirit and scope of invention as defined by the appended claims. As one example, the skin preparation package 28 of FIG. 2 could be located and attached on the exterior of sealing sheet 24 or exterior of outer tray 12 so that it could be accessed even before top sealing-sheet 24 is removed. While the invention is envisioned for use with, and is particularly well suited for, epidural anesthesia, it might find application with other procedures and kits as well.

What is claimed is:

1. An epidural kit for quickly administering epidural anesthesia to a patient, the kit comprising:
   a packaging towel;
   a skin preparation package containing a skin-preparation solution and means for delivering the fluid to the patient's skin, the skin preparation package is ready to be opened and used to prepare a patient's skin for penetration by needles;
   a first syringe pre-filled with a local anesthetic;
   an epidural needle for locating an epidural space of a patient;
   a catheter for positioning in the epidural space of a patient through the epidural needle;
   a second syringe pre-filled with a test fluid;
   a preloaded saline cup having a removable lid and filled with a saline solution;
   a tray for holding and removeably securing the first and second syringes, the epidural needle, and the cup;
   a packaging means for enclosing the tray in a sterile environment; and
   wherein the skin-preparation package is removeably secured relative to the packaging means to allow access to the skin-preparation package without requiring the packaging towel to be unfolded.

2. The kit of claim 1 wherein the packaging means comprises and outer tray with a top sheet.

3. The kit of claim 1 wherein the packaging means comprises an outer tray and a top sheet and wherein the skin-preparation package is removeably secured to an outer portion of the packaging towel where it is immediately available once the top sheet has been removed from the outer tray.

4. The kit of claim 1 wherein the packaging means comprises an outer tray and a top sheet and wherein the skin-preparation package is removeably secured to an exterior surface of the top sheet.

5. The kit of claim 1 wherein the first pre-filled syringe comprises a pre-filled syringe with a needle attached.

6. An anesthesia kit comprising:
   an outer tray having a top portion and an interior portion;
   a packaging towel having an interior and an exterior and disposed within the interior portion of the outer tray;
   a plurality of syringes disposed within the outer tray and on the interior of the packaging towel; and
   a skin-preparation package located on the exterior of the packaging towel to provide for access to the skin-preparation package without requiring access to the interior of the packaging towel.

7. The kit of claim 6 further comprising a cup disposed within the outer tray and on the interior of the packing towel that has a removeably, sealed lid and that is filled with an injectable fluid.

8. The kit of claim 6 further comprising a cup disposed within the outer tray and on the interior of the packing towel that has a removeably, sealed lid and is filled with saline.

9. The kit of claim 6 wherein the plurality of syringes comprise a pre-filled syringe with a local anesthetic and a pre-filled syringe with a test dose.

10. The kit of claim 6 further comprising: a cup disposed within the outer tray and on the interior of the packing towel that has a removeable, sealed lid and is filled with saline; and wherein the plurality of syringes comprise a pre-filled syringe with a local anesthetic and a pre-filled syringe with a test dose.

11. An anesthesia kit comprising:
   an outer tray having a top portion and an interior portion;
   a packaging towel having an interior and an exterior and disposed within the interior portion of the outer tray;
   a skin preparation package removeably secured relative to the outer tray; and
   a plurality of syringes pre-filled with an injectable fluid and disposed within the outer tray and on the interior of the packaging towel.

12. The kit of claim 11 wherein the skin preparation package is located on the exterior of the packaging towel to provide for access to the skin-preparation package without requiring access to the interior of the packaging towel.

13. The kit of claim 11 further comprising a prefilled cup containing an injectable fluid.

14. The kit of claim 12 wherein the skin preparation package is located on the exterior of the packaging towel to provide for access to the skin-preparation package without requiring access to the interior of the packaging towel; wherein the cup is pre-filled with saline; and wherein the plurality of pre-filled syringes comprises a first pre-filled syringe with a local anesthetic.

15. The kit of claim 12 wherein the skin preparation package is located on the exterior of the packaging towel to provide for access to the skin-preparation package without requiring access to the interior of the packaging towel; wherein the cup is pre-filled with saline; and wherein the plurality of pre-filled syringes comprises a first pre-filled syringe with a local anesthetic and a second pre-filled syringe with a test dose.

16. An anesthesia kit comprising:
   an outer tray having a top portion and an interior portion; and
   a first pre-filled non-catheter tip syringe containing an injectable local anesthetic solution and a second syringe pre-filled with a test fluid of a different local anesthetic solution disposed within the outer tray.

* * * * *